(12) United States Patent
Pugia

(10) Patent No.: US 6,228,602 B1
(45) Date of Patent: May 8, 2001

(54) COMPETITIVE APO-PEROXIDASE ASSAY

(75) Inventor: Michael J. Pugia, Granger, IN (US)

(73) Assignee: Bayer Corporation, Elkhart, IN (US)

(*) Notice: Subject to any disclaimer, the term of this patent is extended or adjusted under 35 U.S.C. 154(b) by 0 days.

(21) Appl. No.: 09/415,491

(22) Filed: Oct. 12, 1999

Related U.S. Application Data

(63) Continuation-in-part of application No. 08/990,389, filed on Dec. 15, 1997, now abandoned.

(51) Int. Cl.$^7$ .................... G01N 33/554; G01N 33/53; G01N 33/569; C12N 9/96; C12O 1/28

(52) U.S. Cl. .................... 435/7.32; 435/7.7; 435/7.92; 435/7.1; 435/7.2; 435/7.33; 435/7.37; 435/188; 435/28; 435/4; 436/536; 436/73; 436/74; 436/66

(58) Field of Search .................... 435/7.7, 7.92, 435/7.32, 7.1, 7.2, 7.33, 7.37, 188, 964, 28, 25, 11, 4; 436/66, 536, 73, 74, 904, 543, 800, 805; 424/9.61, 802, 803

(56) References Cited

U.S. PATENT DOCUMENTS

| | | | |
|---|---|---|---|
| 4,208,479 | * 6/1980 | Zuk et al. | 435/7 |
| 4,281,064 | * 7/1981 | Zuk et al. | 435/7 |
| 4,792,521 | * 12/1988 | Shochat | 435/7 |
| 5,089,420 | * 2/1992 | Albarella et al. | 436/66 |
| 5,106,753 | * 4/1992 | Genshaw et al. | 436/74 |
| 5,173,431 | * 12/1992 | Pugia et al. | 436/86 |
| 5,182,213 | * 1/1993 | Genshaw et al. | 436/66 |
| 5,264,348 | * 11/1993 | Schick et al. | 435/28 |
| 5,318,894 | * 6/1994 | Pugia | 435/28 |
| 5,362,633 | * 11/1994 | Pugia | 435/28 |
| 5,374,561 | * 12/1994 | Pugia | 436/98 |
| 5,733,787 | * 3/1998 | Messenger et al. | 436/98 |
| 5,827,880 | * 10/1998 | Malfriy-Camine et al. | 514/492 |

FOREIGN PATENT DOCUMENTS

0525723A2 * 2/1993 (EP).
0525723A3 * 2/1993 (EP).

OTHER PUBLICATIONS

Cochran et al. J. Amer. Chem Soc. 112:9415–9416, 1990.*
Savitsky et al. Appl. Biochem. Biotechnol. 47:317–327, 1994.*
Ugaroa et al. Biochim. Biophys. Acta. 662: 210–219, 1981.*
Motsenbocker et al. J. Biolumin. Chemilum. 9: 7–13, 1994.*
Lebedeva et al. Biokhimiia 42: 1372–1379, Abstract, 1977.*
Claiborne et al. Biochemistry 18: 2329–2335, Abstract, 1979.*
Kelder et al. Biochim. Biophys. Acta 1205: 230–238, Abstract, 1994.*
Quilez et al. FEBS Lett. 395: 73–76, Abstract, 1990.*
Nakanien PK. University of Colorado. Abstracts of the Histochemical Society, 39, p. 717, 1979.*

* cited by examiner

Primary Examiner—Lynette R. F. Smith
Assistant Examiner—S. Devi
(74) Attorney, Agent, or Firm—Jerome L. Jeffers

(57) ABSTRACT

Disclosed is an assay for an analyte in a fluid test sample such as urine which involves combining the fluid test sample with a reagent system comprising an apo-peroxidase, a redox dye, a peroxide and a metal porphyrin which is bound to an analyte/analyte specific binding partner which complex has a combined molecular weight of at least about 180 K Daltons. When this conjugate interacts with analyte in the fluid test sample, a portion of the specific binding partner is dissociated from the complex thereby enabling the metal porphyrin to reconstitute with the apo-peroxidase. The reconstituted peroxidase can interact with the peroxide and redox dye to provide a colored response to analyte in the fluid test sample.

15 Claims, No Drawings

COMPETITIVE APO-PEROXIDASE ASSAY

BACKGROUND OF THE INVENTION

This application is a Continuation-In-Part of application Ser. No. 08/990,389 filed Dec. 15, 1997 now abandoned.

Peroxidase is an enzyme that catalyzes the oxidation of various compounds, such as phenols and amines, by peroxides. Various compounds are referred to as pseudoperoxidases because they behave in a manner similar to the peroxidase enzyme by liberating an electron from hydroperoxides to create an oxidant capable of accepting an electron from a donor species. Accordingly, the pseudoperoxidases are enzyme like in that they catalyze, or otherwise participate in, reactions between peroxides or otherwise oxidizable compounds. The pseudoperoxidases, which include hemoglobin and its derivatives, are collectively referred to as peroxidatively active substances. For example, a peroxidatively active substance, such as hemoglobin and its derivatives, catalyzes the interaction between a hydroperoxide and an oxidizable dye. In such interactions, the peroxidatively active substance imitates the peroxidase enzyme and catalyzes or otherwise participates in an interaction between the oxidizable dye and the peroxide. The oxygen transferred from a peroxide to a peroxidatively active substance creates an oxidant capable of accepting an electron from an oxidizable dye. The resulting interaction provides a detectable response, such as a color transition, wherein the intensity of the response is indicative of the presence or the concentration of the peroxidatively active substance. Suitable oxidizable dyes for use in such an assay include benzidine; o-tolidine, 3,3'5,5;-tetraalkylbenzidine wherein the alkyl groups contain from one to six carbon atoms; 9-dianisidine; 2,7-diaminofluorene; bis-(N-ethyl-quinol-2-one)-azine; (N-methylbenzthiazol-2-one)-(1-ethyl-3-phenyl-5-methyl-triazol-2-one)-azine or a combination thereof. Useful peroxides include hydrogen peroxide, cumene hydroperoxide; 5-butyl hydroperoxide; diisopropylbenzene hydroperoxide; 1-hydroxycyclohexane-1-hydroperoxide; 2,5-dimethyl-hexane-2,5-dihydroperoxide; paramenthane hydroperoxide; 1,4-diisopropylbenzene hydroperoxide; p-5-butyl-isopropylbenzene hydroperoxide; 2-($\alpha$-hydroperoxy-isopropyl)-6-isopropylnaphthalene; tetralin hydroperoxide or a combination thereof.

In U.S. Pat. No. 4,493,890 it is disclosed that glucose oxidase is a conjugated enzyme composed of an enzymatically inactive, high molecular weight protein component (apoenzyme) and FAD (a low molecular weight, nonproteinaceous prosthetic group). Unlike transition metal porphyrins, the flavin adenine dinucleotide (FAD) portion of glucose oxidase does not contain a transition metal. The FAD moiety is sometimes referred to as a prosthetic group because the protein portion of the enzyme forms a complex with this small ligand through high affinity binding. As a result, the prosthetic group becomes an integral part of the protein which is required for the enzyme to function. Apoglucose oxidase and FAD have a high binding affinity (binding constant of about $10^{10}$ molar $^{-1}$) but can be effectively separated by treatment with acidified ammonium sulfate. In U.S. Pat. No. 4,238,565 there is described a specific binding assay wherein FAD is employed as a label and is monitored by its ability to combine with apoglucose oxidase to form active glucose oxidase. In a homogenous assay for determining an antigen in a liquid medium, a test sample of the liquid medium is combined with antibody to the antigen and a labeled conjugate comprising the antigen (or analog thereof) coupled to FAD so that antigen contained in the sample competes with antigen-FAD for binding with antibody. Apoglucose oxidase is also present and is capable of combining with antigen-FAD which is not associated with antibody to yield active glucose oxidase. However, since antibody bound antigen-FAD is not capable of such combination with apoglucose oxidase, the concentration of antigen in the test sample dictates the amount of measurable glucose oxidase which results from the recombination by known methods such as a calorimetric assay. This sort of assay, sometimes referred to as apoenzyme reactivation immunoassay system (ARIS) involves attachment of hapten to the FAD prosthetic group of glucose oxidase which still permits reactivation of the apoglucose oxidase by its interaction with the prosthetic group. However, binding of the anti-hapten antibody to the hapten-FAD conjugate can prevent its association with the apo-glucose oxidase, so that no glucose oxidase activity is observed. Glucose oxidase has been found to be an excellent enzyme for this system since i) the FAD can be dissociated from the intact enzyme to provide a stable apoglucose oxidase, ii) the apoglucose oxidase cannot express enzyme activity but can be easily reconstituted with FAD to the holoenzyme and iii) the parent holoenzyme has a high turnover rate and the $H_2O_2$ reaction product can be determined with high sensitivity by a variety of methods. However, the apoglucose oxidase ARIS method has not been successfully applied in urinalysis due to the presence of FAD derivatives in urine resulting in reconstitution with the apoglucose oxidase to form the active enzyme which can cause false positive assay results. The ARIS systems are not limited by molecular weight of the prosthetic-conjugate:binding partner, i.e. reconstitution occurs regardless of the molecular weight of the binding system. This type of assay is based on binding partner interaction with the prosthetic-conjugate occurring in such an orientation that it causes steric hindrance to reconstitution. This steric hindrance leads to an inhibition that causes the rates of reconstitution to be different between prosthetic conjugate and prosthetic-conjugate binding partner. The difference in reconstitution rates of the two species is used to measure the analyte. Peroxidases also contain a prosthetic group in the form of a transition metal porphyrin which can be separated from the protein to form an apo-peroxidase. The apo-peroxidase system of the present invention is limited by the molecular weight of the analyte/analyte specific binding partner conjugate attached to the metal porphyrin since it was discovered that when this moiety has a total molecular weight of greater than that which will permit the apo-peroxidase and metal porphyrin to recombine, reconstitution with the peroxidase is prevented. Conjugates with a combined molecular weight of greater than about 180 K Dalton have been found to be suitable for preventing reconstitution. The present assay is based on the binding partner:prosthetic conjugate being so large that it prevents reconstitution. Since the binding partner typically has a high molecular weight (antibodies are normally in the 165 K Dalton range) the presence of peroxidase activity can only result from one species, the unbound prosthetic-conjugate, and the activity of this single species is used to measure the analyte.

Steric hindrance to reconstitution requires a specific orientation of the antibody:antigen binding, which orientation is easily developed for small antigens but not for large antigens. Accordingly, the ARIS method is normally limited to small molecular weight antigens of 100 to 1000 g/mol. The present method does not rely on steric hindrance but rather on the molecular weight of the prosthetic-conjugate:binding partner. This technique results in the advantage that the assay is able to detect any size of analyte and eliminates the need to prepare antibodies with a specific binding orientation. Additionally, the present invention, which is based upon the discovery that the size effect can be used to provide an apo-peroxidase system, can be used without measuring rates. This is especially advantageous in urinalysis using test strips since urine strips are usually read visually and visual readings are not readily applicable to rate determination.

The pseudoperoxidases also have prosthetic groups which, when removed, result in an inactive apo- form of the pseudoperoxidase which lacks the peroxidase activity. For example, when iron hematin is separated from hemoglobin, such as by subjecting the hemoglobin to low pH to dissociate the iron hematin followed by filtration to cause the separation of the hematin and apo-hemoglobin, there is provided an inactive form of hemoglobin which may be reactivated by facilitating the reconstitution of the apo-hemoglobin and the iron hematin. The transition metals which constitute part of the metal porphyrin will have a mixture of valences in reagents of the type under consideration.

In Abstracts of the Histochemical Society (1979), Item 39 on page 717 there is discussed an immunoassay using the degree of reconstitution of apoenzymes with active groups in the presence or absence of immuno complexes such as heme-labeled antigen when complexed with antibody will be inhibited from reconstituting with apoperoxidase.

Japanese published patent application 8-224095 discloses an assay system for $Cu^{++}$ in which $Cu^{++}$ is added to apogalactose oxidase in the presence of D-galactose and $O_2$ to produce $H_2O_2$ which reacts with an oxidative condensing agent in the presence of peroxidase to produce a quinoid dye which calorimetrically measures the copper concentration in the fluid sample being tested.

While the use of the heme moiety as a label for apo-peroxidase was theorized by P. K. Nakanein, Univ. of Colo., Abstracts of the Histochemical Society, 39 (1979) where it was suggested that conjugated hematinantigen would not readily intercalate into apo-peroxidase when the antigen was bound to its corresponding antibody, an assay for analytes in fluid test samples employing this principle was never reduced to practice.

SUMMARY OF THE INVENTION

The present invention is an assay for an analyte in a fluid test sample which assay involves combining the fluid test sample with a peroxide, a redox dye, an apo-peroxidase [or apo-pseudoperoxidase] and its corresponding metal porphyrin which is bound to an analyte/analyte specific binding partner complex which complex has a total molecular weight which is sufficiently high to prevent the porphyrin component thereof from recombining with the apo-peroxidase. In this form the apo-peroxidase cannot interact with the peroxide to cause a colored response in the redox dye. However, in the presence of analyte, there is interaction between the analyte and the analyte specific binding partner which disrupts the analyte/analyte specific binding partner complex and thereby reduces the molecular weight of the moiety bound to the metal porphyrin to less than that level at which the reconstitution of the apo-peroxidase and its prosthetic group is inhibited. This allows the apo-peroxidase and the metal porphyrin to reconstitute to form an active peroxidase which can interact with the peroxide and the redox dye to provide a colored response, the intensity of which is directly proportional to the concentration of analyte in the fluid test sample.

The assay of this invention can be used qualitatively or, with the use of appropriate calibration, calorimetric dyes and instrumentation to provide accuracy and precision, semi-quantitative results can be obtained.

DESCRIPTION OF THE INVENTION

Metal-porphyrins are the active center of peroxidatively active proteins and their removal such as by acidification and separation by either ultrafiltration or chromatography results in the formation of apo-peroxidases which have no peroxidase activity but which can be reactivated when mixed with metal-porphyrins, even those which are conjugated to antigens. However, antibody binding to these antigen/metal-porphyrin conjugates prevents reactivation of the apo-peroxidase when this combination exceeds about 180 K Daltons in molecular weight. Free antigen (analyte) in a fluid test sample, to which the antibody bound to the antigen of the antigen/metal porphyrin conjugate has been added, competes for antibody binding thereby freeing the antigen/metal porphyrin conjugate from the antibody in proportion to the analyte present in the fluid test sample. In the case of antigen/metal porphyrin conjugates having a total molecular weight of less than about 180 K Daltons, the antibody free conjugate reactivates the apo-peroxidase to the active form. The activity of the reactivated peroxidase can be detected using a redox indicator and a peroxide at a pH of from 1 to 12 and preferably from 6.5 to 8.5. In this embodiment of the invention, there is provided a test composition comprising:

i) a redox indicator and a peroxide as well as a buffer to maintain the pH at the optimal value, depending upon the metal and redox indicator used, of from 1 to 12;

ii) the specific binding partner (analyte or binding partner therefor)/metal-porphyrin conjugate;

iii) the peroxidatively active substance lacking a prosthetic heme group, i.e. apo-peroxidase; and iv) conjugate binding compounds.

The conjugate binder can take one of two forms:

a) if an antibody is bound to the metal porphyrin, the binder is the antigen or the antigen bound to a larger molecule such as a protein, or b) if an antigen is bound to the metal porphyrin, the binder can be an antibody or an antibody connected to a larger molecule or other biomolecules that bind the antigen can be used. For example, when LPS is the antigen, high density lipoprotein (HDL), which binds LPS, can be used. In the case where IgG is the analyte, the binding partner can be complement factor protein.

Exemplary of antigen/metal-porphyrin conjugates are metals such as Fe, Mn, Cu and Co; porphyrins such as hematin, deuteroporphyrin and coproporphyrin and antigens such as proteins, low molecular weight organics and cell wall components. Examples of apo-peroxidases and pseudoperoxidases which may be used in the present invention are apo-peroxidase, apo-hemoglobin, apo-myoglobin, apo-cyochrome-C, apo-catalase and apo-lactoperoxidase.

This invention involves a dry reagent involving a new calorimetric technology based on a competitive apo-peroxidase chemistry which is useful for measuring small and large molecular weight components in biological fluids such as blood and urine. Typical analytes involve drugs, proteins and cells, i.e. gram positive and gram negative bacterial cells. The invention is based on the discovery that metal-porphyrin conjugates will not intercalate into apo-peroxidases when bound by a conjugate binder as long as the conjugate:binder complex has a molecular weight of greater than about 180,000 g/mol. It was found that conjugation of compounds up to a molecular weight of an antibody (160,000 g/mol) did not interfere with apo-peroxidase reactivation, so that the conjugate:binder complex can be an antigen:antibody complex wherein the antigen is the analyte whose presence or concentration is being sought and the antibody is a specific binding partner for the analyte. Specific binding partners other than antibodies include avidin/biotin pairs. The metal porphyrin conjugate can, for example, be comprised of an antibody and metal hematin wherein the conjugate binder (ligand) would be an antigen which is the analyte or derivative thereof recognized by the antibody and the analyte is the antigen recognized by the antibody. When the antibody antigen combination has a combined molecular weight of greater than about 180 K Daltons it cannot intercalcate with the apo-peroxidase and a peroxidase catalyzed reaction does not result. However, when the conjugate, conjugate binder, apo-peroxidase and a hydroperoxide are combined with a fluid test sample containing analyte, there takes place a competitive reaction in which analyte in the sample competes for binding with the antibody bound to antigen on the conjugate, and, to the extent that this competition strips antibody from the conjugate, thereby lowering its molecular weight to below about 180 K Daltons, the conjugate can combine with the apo-peroxidase to provide an active enzyme which will catalyze the reaction needed to provide the detectable response. The magnitude of this response will be proportional to the concentration of analyte in the test fluid which concentration can be determined by comparison with calibration charts prepared using known concentrations of analyte. A similar response will be observed when the metal porphyrin is conjugated with an antibody specific for the antigen (analyte) and the binder is the analyte or analyte derivative.

The method of practicing the present invention is further illustrated by the following procedures and examples.

A. Procedure for Preparing Reagent Used in Examples IV to VII

Dry reagent paper was prepared through sequential impregnations of Whatman 3MM with an aqueous first dip and an ethanol second dip using dryer temperatures of 100° C. for 7 minutes. The first dip contained buffer while the second dip contained the redox indicator, TMB, and the hydroperoxide, DBDH.

The first dip consisted of 10 mL of 73 mg/dL hematin-IgG, 1.0 mL of 10 mg/mL mouse anti-human kappa chain monoclonal antibody, 0.66 g glycerol-2-phosphate, 4.2 µM apo-hemoglobin, 0.63 g 4-morpholine propane sulfonic acid (MOPS) as buffer and 0.11 g of sodium dodecyl sulfate (SDS) as surfactant. The pH was adjusted to 7.5 with 1N NaOH.

The second dip contained 2.5 g of polyvinylpyrolidone, 1.6 g DBDH and 0.795 g TMB in 100 mL ethanol.

The preferred concentration and allowable range of each dip component are set out in Table 1:

TABLE 1

APO-PEROXIDASE REAGENT

| | Preferred Concentration | Allowable Range |
|---|---|---|
| First Dip (aqueous) | | |
| Glycerol-2-Phosphate | 225 nM | 0–800 mM |
| MOPS | 225 mM | 0–800 mM |
| SDS | 28 mM | 8–100 mM |
| Fe-HEDTA (ascorbate scavenger) | 7.5 mM | 0–20 mM |
| Triisopropylamine borate (stabilizer) | 33 | 0–120 |
| Fe Hematin-antigen (metal porphyrin conjugate) | 3.2 µM | 1–20 µM |
| Ab (competitive binder) | 4.4 µM | 1–20 µM |
| Apo-hemoglobin (Apo-peroxidase) | 4.2 µM | 1–20 µM |
| Adjust pH with 1N NaOH | 7.5 | 1–12 |
| Second Dip (ethanol) | | |
| Polyvinylpyrrolidone | 2.5 w % | 0–7.5 w % |
| Tetramethylbenzidine (TMB) | 33 mM | 5–100 mM |
| Diisopropyl benzene dihydroperoxide (DBDH) | 66 mM | 5–150 mM |
| Orange G dye (Background dye) | 0.20 mM | 0–5 mM |
| Ethyl Orange dye (Background dye) | 0.20 mM | 0–5 mM |

B. The reagent papers produced from the above dips were cut into strips and dipped into urine containing various hematins from a urine pool of 1.015 specific gravity. The reflectance at 660 nm, measured using a CLINITEK™-200+ instrument, obtained one minute after dipping, was taken as representative of reagent activity.

EXAMPLE I

Detection Limit Study

In this example apo-peroxidase is compared to hematin and hematin-antigen conjugates to determine the detectable concentrations and effects of conjugation and antigen molecular weight on apo-enzyme reactivations. Solutions containing combinations of apo-POD, $Fe^{+3}$ hematin and hematin conjugate were tested for peroxidase activity. Peroxidase activity was measured in urine using HEMASTIX® reagent as set out in Table 3. This reagent is similar to that set out in Table 1 but lacking the metal porphyrin conjugate, competitive binder and apo-peroxidase while containing lepidine as an activator. The results of this detection limit study are set out in Table 2.

TABLE 2

| | | Mean % Reflectance @ 660 nm (1 minute @ 30° C.) | | |
|---|---|---|---|---|
| Case | Composition Conc: | 3.6 mM | 3.6 nM | 3.6 nM |
| A | hematin | 65.1 | 64.9 | 63.4 |
| C | apo-POD, hematin | 55.3 | 46.3 | 48.9 |
| E | apo-POD | 64.1 | 62.3 | 61.2 |
| | antigen: | BJP | IgG | Sulfmethazine |
| | Molecular Wt. | 23,000 | 160,000 | 278 |
| B | Antigen-hematin | 65.8 | 67.0 | 64.5 |
| D | apo-POD, antigen-hematin | 49.1 | 39.9 | 42.3 |

The peroxidase activity of hematin (Case A) or antigen hematin conjugate (Case B) was not detectable at a concentration of 3.6 nM. The apo-POD also demonstrated no activity by itself (Case E) whereas the peroxidase activity of hematin (Case C) and antigen-hematin conjugate (Case D) was detectable at 3.6 nM in the presence of apo-POD. This example demonstrates that detection of nM quantities via peroxidase reactivation is possible with the redox indicator and hydroperoxide technology which has a turn over rate of $10^5$ moles of DBDH/min and a dye (TMB) molar extinction of $10^5$. Conjugation of the hematin with antigen did not interfere with the apo-enzyme reactivation. In fact, in the antigen hematin conjugates of Case D, the reactivation caused a response as great as 25.0% R at 1 minute, as can be determined by comparing 3.6 nM apo-peroxidase (Case E) to 3.6 nM apo-peroxidase:antigen-hematin (Case D). Surprisingly, conjugation of antigens up to a molecular weight of 160,000 g/mol (in the case of IgG) did not prevent reactivation of the apo-POD. Reactivation was complete in 1 minute (demonstrating the short equilibrium times) and was not dependent upon temperatures from 20–40° C. or apo-POD concentration.

Procedure for Detection Limit Experiment

A 10 µL portion of hematin (3.6 µM, 0.23 mg/dL in phosphate buffered saline) or a 10 µL hematin-BJP allotment (3.6 µM, 8.61 mg/dL in phosphate buffered saline) was mixed with 10 µL apo-POD (3.6 µM, 14.0 mg/dL in phosphate buffered saline) all in 980 µL of phosphate buffered saline and then diluted to the desired concentration with additional phosphate buffered saline. The solution was incubated for 1 minute at 40° C. or at room temperature. The response of HEMASTIX® reagent dipped into the test solution was measured on a CLINITEK™-200 reflectance instrument. The response of the reagent set out in Table 1 on the phosphate buffered solution alone was 65.2% reflectance at 1 minute.

Apo-horse radish peroxidase was obtained from Sigma Chemical Company of St. Louis, Mo. The phosphate buffered solution was prepared by adding 0.69 g monobasic sodium phosphate, 0.71 g of dibasic sodium phosphate and 0.45 g of sodium chloride to 100 mL of water.

Procedure for Antigen Response Experiment

A 10 $\mu$L sample of hematin-BJP[1] (3.6 $\mu$M, 8.61 mg/dL in phosphate buffered saline), anti-BJP (3.6 $\mu$M, 52.56 mg/dL in PBS) and BJP (3.6 $\mu$M, 8.28 mg/dL in phosphate buffered saline) were mixed with 10 $\mu$L apo-POD (3.6 $\mu$M, 14.0 mg/dL in phosphate buffered saline) and 960 L phosphate buffered saline. The solution was incubated for 5 to 10 minutes at room temperature and the response to HEMASTIX® reagent dipped in the test solution was measured using a CLINITEK®-200 instrument. The response of HEMASTIX® reagent with the phosphate buffered saline solution containing hematin alone was 65.7% reflectance at 1 minute. Sheep anti-human BJP monoclonal antibody was obtained from The Binding Site Limited of Birmingham, England.

[1] BJP=Bence Jones Protein

The HEMASTIX® reagent referred to earlier with the addition of lepidine and at a lower pH when compared to the formula of Table 1 was applied to the strip in a two dip system of the following composition and used in Examples I to IV (Table 3).

EXAMPLE II

Proximity Effect

In this example, antibody binding of the hematin-antigen conjugate is shown to prevent apo-enzyme reactivation (Table 4). The data set out in Table 4 were generated by using the HEMASTIX® formula with lepidine but lacking apo-peroxidase, antigen-hematin antigen and antibody. The later were mixed in solution and reagent strips with the modified HEMASTIX® formula were immediately dipped into the solution and read using a CLINITEK™-200+ reflectance spectrometer.

The prevention of apo-enzyme reactivation was observed as long as the [hematin] antigen/antibody complex had a molecular weight of greater than 180,000 g/mol. Accordingly, sulfamethazine plus antibody (mol wt. ≈161,000) did not prevent apo-enzyme reactivation. However, attachment of sulfmethazine to polyacrylic acid (PAA) (mw=200,000 g/mol) did prevent reactivation of the apo-enzyme as shown by 51.5%R observed for run 10. It was also shown that an antigen (IgG-mol. wt. 160,000 and BJP-mol. wt. 23,000) could be detected in urine by its ability to free hematin-antigen[antibody] conjugate to reactivate apo-POD by breaking the binding between antigen and antibody.

TABLE 4

| Run | Antigen | APO-Peroxidase | Antigen-Hematin | [Antigen] | Antibody | Reagent Response (% R @ 30 Sec) @ 660 nm |
|---|---|---|---|---|---|---|
| 1 | BJP | 36 nM | 36 nM | None | 36 nM | 43.1 |
| 2 | BJP | 36 nM | 36 nM | 12 nM | 36 nM | 33.7 |
| 3 | BJP | 36 nM | 36 nM | 24 nM | 36 nM | 26.6 |
| 4 | BJP | None | 36 nM | 36 nM | 36 nM | 41.7 |
| 5 | BJP | 36 mM | 36 nM | None | None | 24.2 |
| 6 | IgG | 36 nM | 36 nM | None | 36 nM | 42.4 |
| 7 | IgG | 36 nM | 36 nM | 24 nM | 36 nM | 19.2 |
| 8 | Sulfamethazine | 36 nM | 36 nM | None | 36 nM | 23.6 |
| 9 | Sulfamethazine | 36 nM | 36 nM | 24 nM | 36 nM | 21.3 |
| 10 | Sulfmethezine PAA | 36 nM | 36 nM | None | 36 nM | 51.5 |
| 11 | Sulfmethazine PAA | 36 nM | 36 nM | 24 nM | 36 nM | 49.2 |

TABLE 3

| | Allowable Concentration | Range |
|---|---|---|
| First Dip (Aqueous) | | |
| Glycerol-2-Phosphate | 225 mM | 0–800 mM |
| MOP | 225 mM | 0–800 mM |
| SDS | 28 mM | 8–100 mM |
| Triisopropylamine borate | 33 mM | 0–120 mM |
| Fe-HEDTA | 7.5 mM | 0–20 mM |
| Adjust pH with 1N NaOH | 6.3 | 5.5–8.5 |
| Second Dip (Ethanol) | | |
| Polyvinylpyrrolidone | 2.5 w % | 0–7.5 w % |
| Tetramethylbenzidine [TMB] | 33 $\mu$M | 5–100 mM |
| Diisopropyl Benzene Dyhydroperoxide [DBDH] | 66 mM | 5–150 mM |
| Lepidine | 100 mM | 5–150 mM |
| Orange G dye (background dye) | 0.20 mM | 0–5 mM |
| Ethyl Orange dye (background dye) | 0.20 mM | 0–5 mM |

EXAMPLE III

Interference Study

In this example, a peroxidase detecting dry reagent with resistance to 0.81 mg/dL hemoglobin (or myoglobin) and 25 mg/dL ascorbate and sufficient sensitivity to detect apo-peroxidase reactivation was used. The peroxidase detecting reagent was made by removing lepidine activator in the HEMASTIX® reagent and increasing the pH to 7.5. Without modification, hemoglobin (or myoglobin) causes a false positive response. Ascorbate does not cause a false negative response in the system due to the use of an ascorbate scavenger system.

The reagent was tested by dipping it into solutions containing the interfering substance with and without Fe hematin. These formulation changes to the HEMASTIX® reagent also reduced the sensitivity of the reagent needed to detect apo-peroxidase reactivation from 3 nM in Example I to 12 $\mu$M in this Example III. As expected, the 12 $\mu$M hematin was activated by the addition of 12 $\mu$M apo-POD. The results of this interference study are set out in the following Table 5.

TABLE 5

| Reagent | Water | | 0.81 mg/dL Mb | | 0.81 mg/dL Hb | | 25 mg/dL Ascorbic | |
|---|---|---|---|---|---|---|---|---|
| | Mean | SD | Mean | SD | Mean | SD | Mean | SD |
| HEMASTIX ® (lepidine/pH 6.3) | 63.6 | 3.1 | 5.1 | 2.7 | 3.0 | 0.4 | 66.4 | 4.5 |
| +3.6 µM Fe Hematin | 8.8 | 1.9 | | | | | | |
| +12 µM Fe Hematin | 6.4 | 1.0 | | | | | 5.3 | 0.6 |
| +12 µM Fe Hematin/12 µM apo-POD | 4.1 | 0.4 | | | | | | |
| +36 µM Fe Hematin | 3.1 | 1.4 | | | | | | |
| HEMASTIX ® (no lepidine/pH 7.5) | 77.4 | 1.7 | 78.2 | 1.6 | 76.5 | 1.2 | 79.4 | 2.3 |
| +3.6 µM Fe Hematin | 79.2 | 1.3 | | | | | | |
| +12 µM Fe Hematin | 72.4 | 3.0 | | | | | 73.2 | 3.1 |
| +12 µM Fe Hematin/12 µM apo-POD | 54.0 | 5.7 | | | 55.3 | 3.4 | | |

From Table 5 one can determine that HEMASTIX® with lepidine is interfered with by hemoglobin or myoglobin as shown by 5.1% and 3.0% responses verses 78.2 and 76.5.

EXAMPLE IV

Metal Porphyrin Study

In this example, other metal porphyrins were tested for their ability to reactivate different types of apo-peroxidases. Metals such as Fe, Cu, Mg, Zn, Ni, Mn, Co and Pd were complexed to hematin and added to the peroxidase detecting agent. Metals such as Mn, Fe, Cu and Co and porphyrins other than hematin, i.e. deuteroporphyrin and coproporphyrin were also shown to provide the desired response. This is illustrated in Table 6 by the combination of apo-peroxidase with iron and manganese porphyrin resulted in color formation (lower % R) as compared to water. An apo-pseudoperoxidase, apo-hemoglobin, was shown to work in this experiment.

TABLE 6

| | % R @ 90 second read time on CLINITEK ™ -200+ | | | | | |
|---|---|---|---|---|---|---|
| | Water | | 12 µM apo-POD | | 12 µM apo-Hb | |
| Reagent | Mean | SD | Mean | SD | Mean | SD |
| HEMASTIX ® (no lepitine/pH 7.5) | Column 1 | | Column 2 | | Column 3 | |
| +12 µM Fe Hematin | 71.5 | 1.9 | 50.9 | 4.2 | 45.3 | 1.2 |
| +12 µM Fe coproporphyrin | 69.7 | 1.1 | 56.4 | 3.6 | 52.1 | 3.5 |
| +12 µM Fe deuteroporphyrin | 72.2 | 3.1 | 56.1 | 5.2 | 49.2 | 2.3 |
| +120 µM Mn deuteroporphyrin | 66.4 | 3.2 | 48.2 | 4.3 | — | — |
| +120 µM Co deuteroporphyrin | 71.5 | 2.2 | 74.1 | 1.4 | — | — |
| +120 µM Mg deuteroporphyrin | 74.4 | 1.3 | 70.9 | 2.9 | — | — |
| +120 µM Pb deuteroporphyrin | 72.1 | 1.9 | 73.4 | 1.9 | — | — |
| +120 µM Ni deuteroporphyrin | 75.5 | 2.4 | 76.1 | 2.1 | — | — |
| +120 µM Zn deuteroporphyrin | 71.3 | 1.5 | 70.7 | 1.8 | — | — |
| +120 µM Cu deuteroporphyrin | 73.7 | 3.9 | 57.2 | 1.2 | — | — |

The data of Table 6 demonstrate that no metal porphyrin is detected without apo-peroxidase or apo-hemoglobin as shown by the percent reflectance in Column 1 being ≧66% R. The addition of either apo-peroxidase or apo-hemoglobin causes a colored response as shown by % R of ≦56 in Columns 1 and 3. The response is similar for three different porphryins. The use of Mn and Cu resulted in responses similar to those obtained for Fe as shown in Column 2. The other metals were not active in this system since the activity of the metal is dependent on the particular peroxide, pH and redox indicator used.

EXAMPLE V

Complete Dry Reagent—for IgG

In this example, the ascorbate and hemoglobin resistant reagent for detecting peroxidase reactivity was combined with apo-hemoglobin; Fe hematin conjugated to human IgG and anti-human IgG into one reagent (Table 1). As demonstrated by Table 7, the complete reagent detected IgG in urine with good correlation between the concentration of IgG in the test solution and the response recorded.

TABLE 7

| | % R @ 90 sec read time on CLINITEK ™-200+ | | | | | | | |
|---|---|---|---|---|---|---|---|---|
| | 0 µM IgG | | 12 µM IgG | | 24 µM IgG | | 36 µM IgG | |
| Reagent | Mean | SD | Mean | SD | Mean | SD | Mean | SD |
| Apo-peroxidase | 61.2 | 3.5 | 55.3 | 1.2 | 49.5 | 3.4 | 42.3 | 4.6 |

Reagent contained 12 µM Fe Hematin-IgG, 12 µM anti IgG and 12 µM apo-hemoglobin

EXAMPLE VI

Complete Dry Reagent for Gram Negative Cells

In this example, the ascorbate and hemoglobin resistant reagent for detecting peroxidase activity was combined with apo-hemoglobin; Fe hematin conjugated to LPS and an antibody specific to an anti-rabbit bacterial lipopolysaccharide (LPS) into one reagent. The Fe-hematin-LPS conjugate was made up of 16.3 LPS molecules attached to oval albumin along with 5.2 hematin molecules. As demonstrated by Table 8, the complete reagent detected bacterial cells in urine with three species of gram negative cells being detected. Since all gram negative cells have LPS on their surfaces, this technique provides a screen for gram negative urinary tract infections. A specimen containing gram negative cells would disrupt the binding of the LPS conjugate to antibody as the LPS of the gram negative cells binds to the antibody. The LPS conjugate is then free to reconstitute with apo-hemoglobin to form its active form to generate a detectable response.

TABLE 8

| % R @ 650 nm and 90 Sec Read Time on CLINITEK ™ 200+ | | | | |
| --- | --- | --- | --- | --- |
| Organism (cells/µl) | 0 | 10³ | 10⁵ | 10⁷ |
| *Proteus mirabilis* (ATCC 25933) | 65.0 | | 58.7 | 44.8 |
| *Pseudomonas aeruginosa* (ATCC 9027) | 71.5 | 53.3 | 48.5 | 38.2 |
| *E. coli* (ATCC 8739) | 66.0 | | 60.2 | 49.9 |

The antibody was rabbit anti-*E. coli* LPS; catalog #YBDB30506R: Lot #G4520; neat antisera; Accurate Chemical & Scientific Corporation of Westbury, N.Y.

The following experimental methods were used in the foregoing examples:

Procedure for Preparation of Conjugate

A 868 µM solution of hematin in 0.1 N NaOH (55 mg/dL, 633.51 g/mol) was added to a 858 µM solution of 1,3-dicyclohexyl carbodiimide in acetonitrile (19.4 mg/dL, 226 g/mol) and stirred for five minutes at room temperature. A solution containing 25 µM of the activated hematin and 12 µM antigen (either human kappa Bence Jones Protein (BJP) at 30 mg/dL or human gamma globulin (IgG) at 200 mg/dL) was made and stirred for an additional five minutes at room temperature. The hematin-antigen conjugate was separated from the free antigen by centrifugation to dryness using an Amicon Ultra filtration membrane followed by several washings with deionized water. Hematin conjugate is more reluctant to pass through the membranes than IgG or BJP resulting in the conjugate being collected on the membrane. After the final washing, the hematin-antigen conjugate was dissolved in 175 mL of deionized water. The reaction was found to be greater than 64% complete by protein determination using the coomassie brilliant blue method and contained 128 mg of protein/4.3 µM conjugate.

The coomassie brilliant blue method was performed by adding 30 µL of sample to 1.5 mL of Bradford reagent (0.01 g coomassie brilliant blue, 10 mL 85% phosphoric acid, 5 mL ethanol and 85 mL water) and measuring absorbance at 590 nm and comparing the absorbance to a standard curve of protein concentration.

Procedure for Making Apo-hemoglobin

A 0.7% solution of hemoglobin was lowered to pH 1.5 and the resulting solution was ultrafiltered through a 10 KDa cutoff membrane followed by several changes of water. Filtered material was reconstituted into water. The apo-hemoglobin passed through the filter while the dark Fe++ hematin and hemoglobin remained behind. The filtrate, 440 mL of which was collected, was found to contain 430 mg of protein (apo-hemoglobin) by assay or 23 µM. The HEMAS-TIX® result was + for this solution indicating that the amount of hemoglobin was low. The collected fraction which did not pass through the filter was dissolved in 75 mL of water and was found to contain 270 mg of protein by assay. It produced a HEMASTIX® result of +++++ indicating a high concentration of hemoglobin.

What is claimed is:

1. An assay for an analyte in a fluid test sample which comprises combining the fluid test sample with a peroxide and a redox dye, together with an apo-peroxidase or apo-pseudoperoxidase and a metal porphyrin which is bound to an analyte/analyte specific binding partner complex, said complex having a combined molecular weight of at least about 180 K Daltons which is sufficiently high to prevent reconstitution of the apo-peroxidase or apo-pseudoperoxidase and metal porphyrin in the absence of analyte but will allow such reconstitution in the presence of analyte in the fluid test sample due to interaction between the analyte in the fluid test sample and the analyte specific binding partner portion of the complex which disrupts the complex to thereby reduce the molecular weight of the analyte/analyte specific binding partner complex bound to the metal porphyrin to less than that level at which the reconstitution of the apo-peroxidase and metal porphyrin is inhibited so that the apo-peroxidase and its corresponding metal porphyrin can reconstitute to form an active peroxidase which will interact with the peroxide and the redox dye at a pH of from about 1 to 12 to provide a colored response.

2. The assay of claim 1 wherein the analyte/analyte specific binding partner complex is bound to the metal porphyrin through the analyte specific binding partner.

3. The assay of claim 1 wherein the analyte specific binding partner is an antibody or a fragment thereof.

4. The assay of claim 1 wherein the analyte/analyte specific binding partner complex is bound to the metal porphyrin through the analyte.

5. The assay of claim 3 wherein the analyte is a bacterial cell or a portion thereof.

6. The assay of claim 5 wherein the bacterial cell portion is lipopolysaccharide (LPS) or lipoteichoic acid (LTA).

7. The assay of claim 1 wherein the peroxide is hydrogen peroxide, cumene hydroperoxide; 5-butyl hydroperoxide; diisopropylbenzene hydroperoxide; 1-hydroxycyclohexane-1-hydroperoxide; 2,5-dimethylhexane-2,5-dihydroperoxide; paramenthane hydroperoxide; 1,4-diisopropylbenzene hydroperoxide; p-t-butyl-isopropylbenzene hydroperoxide; 2-(α-hydroperoxyisoporopyl)-6-isopropylnaphthalene; tetralin hydroperoxide or a combination thereof.

8. The method of claim 1 wherein the dye is benzidine; o-tolidine, 3,3',5,5'-tetraalkylbenzidine wherein the alkyl groups contain from one to six carbon atoms; 9-dianisidine; 2,7-diaminofluorene; bis-(N-ethylquinol-2-one)-azine; (N-methylbenzthiazol-2-one)-(1-ethyl-3-phenyl-5-methyltriazol-2-one)-azine or a combination thereof.

9. An assay for an analyte in a fluid test sample comprising combining the fluid test sample with a reagent system comprising a hydroperoxide, and a redox dye together with an apo-peroxidase and a metal porphyrin bound to an analyte/analyte specific binding partner complex which analyte/analyte specific binding partner conjugate has a molecular weight of at least about 180 K Daltons to cause the apo-peroxidase and metal porphyrin to recombine to form an active peroxidase in the presence of analyte in the fluid test sample so that it can interact with the hydroperoxide and redox dye to provide a colored response.

10. An assay for the presence of bacterial cells which are cells of gram negative bacteria characterized by having lipopolysaccharide (LPS) on the cell surface or gram positive bacteria having lipoteichoic acid (LTA) on the cell surface in a fluid test sample which assay comprises combining the fluid test sample with a peroxide and a redox dye together with an apo-peroxidase or an apo-pseudoperoxidase and a metal porphyrin which is conjugated to a LPS and anti-LPS or a LTA and anti-LTA complex which complex prevents reconstitution of the apo-peroxidase or apo-pseudoperoxidase and metal porphyrin in the absence of the bacteria but allows such reconstitution in the presence of the bacteria in the fluid test sample due to interaction between the bacteria and the anti-LPS or anti-LTA which disrupts the conjugate thereby allowing the metal porphyrin to reconstitute with the apo-peroxidase or apo-pseudoperoxidase to form an active peroxidase or pseudoperoxidase which can interact with the peroxide and the redox dye at a pH of from 1 to 12 to provide a colored response which colored response is indicative of the presence of the bacteria in the fluid test sample.

11. The assay of claim 10 wherein the bacteria are gram negative having LPS on its cell surface.

12. The assay of claim 10 wherein the test sample is urine.

13. The assay of claim 11 wherein the gram negative bacteria are *Proteus mirabilis, Pseudomonas aeruginosa* or *E. coli.*

14. The assay of claim 13 wherein the bacteria are gram positive having lipoteichoic acid (LTS) on their surface.

15. The assay of claim 11 wherein the fluid test sample is urine.

* * * * *